United States Patent
Bohlmann et al.

(10) Patent No.: US 7,361,645 B2
(45) Date of Patent: Apr. 22, 2008

(54) ANDROGENIC 7-SUBSTITUTED 11-HALOGEN STEROIDS

(75) Inventors: Rolf Bohlmann, Berlin (DE); Hermann Kuenzer, Berlin (DE); Reinhard Nubbemeyer, Belin (DE); Dieter Zopf, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 590 days.

(21) Appl. No.: 10/467,352

(22) PCT Filed: Jan. 24, 2002

(86) PCT No.: PCT/EP02/00722

§ 371 (c)(1), (2), (4) Date: Feb. 4, 2002

(87) PCT Pub. No.: WO02/059139

PCT Pub. Date: Aug. 1, 2002

(65) Prior Publication Data

US 2005/0075322 A1    Apr. 7, 2005

(30) Foreign Application Priority Data

Jan. 24, 2001    (DE) ................................ 101 04 327

(51) Int. Cl.
*A61K 31/56*    (2006.01)
*C07J 1/00*    (2006.01)

(52) U.S. Cl. ........................ 514/178; 552/644; 552/647

(58) Field of Classification Search ................ 514/178; 552/644, 647

See application file for complete search history.

(56) References Cited

U.S. PATENT DOCUMENTS

| 3,665,021 | A |   | 5/1972 | Elks et al. |
| 3,966,713 | A | * | 6/1976 | Hofmeister et al. ........ 514/172 |
| 4,873,233 | A | * | 10/1989 | Villa et al. .................. 514/179 |
| 5,952,319 | A |   | 9/1999 | Cook et al. |
| 6,369,047 | B2 | * | 4/2002 | Cook et al. ................. 514/179 |
| 6,710,039 | B1 | * | 3/2004 | Ring et al. .................. 514/178 |
| 6,881,728 | B1 | * | 4/2005 | Loozen et al. .............. 514/177 |

FOREIGN PATENT DOCUMENTS

| DE | 24 10 442 A | 9/1975 |
| FR | 1 489 519 A | 7/1967 |
| GB | 863 661 A | 3/1961 |
| GB | 1 260 463 A | 1/1972 |
| WO | WO 00 59920 A | 10/2000 |

OTHER PUBLICATIONS

R. Hampl et al., "Iodo derivative of testosterone as potential biological markers"; J. Steroid Biochem. (1980); 13(9); 1035-8; XP008004097; p. 1037; Table 3, (To the extent considered by the international search report).

* cited by examiner

*Primary Examiner*—Barbara P. Badio
(74) *Attorney, Agent, or Firm*—Millen, White, Zelano, Branigan, P.C.

(57) ABSTRACT

The invention relates to 11β-halogen steroids with general formula (I), whereby $R^{11}$ is halogen, X—Y-Z represents a group with one of the two structures CH=C—C or $CH_2$—C=C and the other radicals have the meaning that is indicated in the claims, also the production and use of these compounds for the production of pharmaceutical agents as well as pharmaceutical preparations that contain 11β-halogen steroids.

20 Claims, 4 Drawing Sheets

ANDROGENIC 7-SUBSTITUTED 11-HALOGEN STEROIDS

The invention relates to 11β-halogen steroids, their production and use for the production of pharmaceutical agents, pharmaceutical preparations that contain 11β-halogen steroids as well as the use of certain 11β-halogen steroid derivatives as a component of compounds with androgenic action.

For therapy of male menopause and for development of male sex organs as well as for male birth control, androgens, especially testosterone, are used. In addition, these hormones also have partial anabolic active components that promote, i.a., muscle growth.

Male menopause is characterized by an age-related reduction in endogenous androgen production, so that hormone replacement (HRT: hormone replacement therapy) is performed for treatment thereof.

In addition to a reduction of spermatogenesis, the LH-RH administration for male birth control also results in the release of LH and in reducing testosterone levels and libido, which are compensated for by administration of testosterone pharmaceutical agents (D. E. Cummings et al., "Prostate-Sparing Effects of the Potent Androgen 7α-Methyl-19-Nortestosterone: A Potential Alternative to Testosterone for Androgen Replacement and Male Contraception," Journal of Clinical Endocrinology and Metabolism, Vol. 83, No. 12, pages 4212-4219 (1998)).

Combinations including an androgen and a progestogen can be used to control male fertility (c.f. for instance WO 01/60376 and the references cited therein).

In the case of treatment with testosterone, it has been shown that side effects occur, especially an enlargement of the prostate owing to an increase in the number of cells and glands of the stroma (BPH: benign prostate hyperplasia). In the metabolism of testosterone that is mediated by 5α-reductase, dihydrotestosterone (DHT) that can result, i.a., in the occurrence of BPH is produced (Cummings et al., ibid.; WO 99/13883 A1). The inhibition of the 5α-reductase is therefore used for treating BPH in clinical practice (finasterides).

The quick metabolism of the androgenic steroid testosterone in the human body further results not only in the formation of undesirable DHT, but also in that an oral administration of higher doses is necessary to reach the desired effect level of testosterone. Alternative forms for dispensing, such as i.m.—injections or large patches, are therefore necessary.

To replace testosterone in the above-mentioned indication areas, 7α-methyl-19-nortestosterone (MeNT) was proposed which has, on the one hand, a higher biological effectiveness as testosterone, since it has a higher binding affinity to the androgen receptors. On the other hand, because of a steric inhibition by the 7α-methyl group, it presumably resists metabolization by 5α-reductase (Cummings et al., ibid., WO 99/13883 A1, WO 99/13812 A1, U.S. Pat. No. 5,342,834).

During metabolism of testosterone, a smaller portion of this compound is also reacted by aromatization of ring A of the steroid system to form estradiol, especially in the brain, in the liver and in the fatty tissue. With respect to the total action of the testosterone and its metabolites, estradiol is substantially responsible for sex-specific behavior and gonadotrophin regulation. Therefore, its action just like that of testosterone for the adult male is regarded as advantageous (Cummings et al., ibid.).

It has been shown, however, that the pharmacokinetics of testosterone is not satisfactory. In particular in the case of oral dispensing, testosterone is quickly excreted again, so that the effectiveness and the duration of action of the thus produced pharmaceutical agents is unsatisfactory. Other testosterone derivatives were therefore also synthesized. Such derivatives are described in, i.a., U.S. Pat. No. 5,952,319, in particular 7α-,11β-dimethyl derivatives of 19-nortestosterone, namely 7α,11β-dimethyl-17β-hydroxyestr-4-en-3-one, 7α,11β-dimethyl-17β-heptanoyloxyestr-4-en-3-one, 7α,11β-dimethyl-17β-[[(2-cyclopentylethyl)-carbonyl]-oxy]-estr-4-en-3-one, 7α,11β-dimethyl-17β-(phenylacetyloxy]-estr-4-en-3-one and 7α,11β-dimethyl-17β-[[(trans-4-[n-butyl]cyclohexyl)-carbonyl]-oxy]-estr-4-en-3-one.

The above-mentioned 7α,11β-dimethyl-derivatives have the above-mentioned advantages, like MeNT, including an improved pharmacokinetics, i.e., its effectiveness and duration of action are improved relative to testosterone. These derivatives, however, can be produced only via an expensive synthesis method.

The problem on which the invention is based is therefore to find derivatives of testosterone that are not sensitive relative to a reduction by means of 5α-reductase, that also have an improved pharmacokinetics compared to 7α-methyl-19-nortestosterone and that can be produced easier than the 7α,11β-dimethyl-derivatives at the same time.

The problem on which this invention is based is solved by 11β-halogen steroids according to claim 1, by the use of 11-β-halogen steroids as a component of compounds with androgenic action according to claim 9, also by a process for the production of these compounds according to claim 10, a use of these steroids for the production of pharmaceutical agents according to claim 11 as well as by pharmaceutical preparations according to claim 12. Preferred embodiments of the invention are indicated in the subclaims.

As components of compounds with androgenic action, the 11β-halogen steroids according to the invention have the following basic structure:

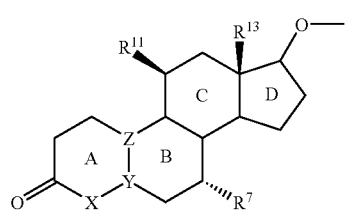

whereby X—Y-Z represents a group with one of the two structures CH=C—C or $CH_2$—C=C, the other bonds are saturated in ring A, $R^7$ and $R^{13}$ are not hydrogen, and $R^{11}$ is a halogen.

In the other positions on the ring skeleton, any other substituents including hydrogen consequently can be present.

The invention thus basically relates to the following two basic structures, namely 11β-halogen-estr-5(10)-en-3-one:

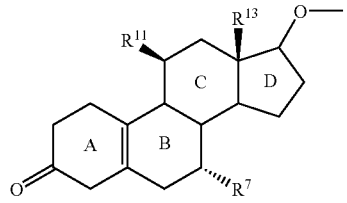

as well as 11β-halogen-estr-4-en-3-one:

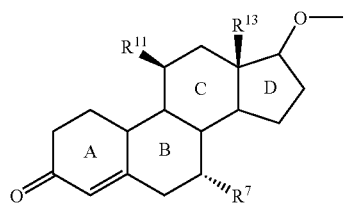

In particular, the androgenic steroids according to the invention have the following general formula I:

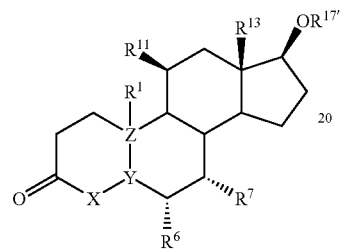

in which

X—Y-Z represents a group with one of the two structures CH=C—C or CH$_2$—C=C $R^1$ can be in α- or β-position, and stands for hydrogen, R or P-Q-R that is bonded via P to the basic ring structure, whereby P and Q represent straight-chain or branched-chain, optionally partially or completely fluorinated $C_1$ to $C_8$ alkylene, -alkenylene, -alkinylene groups and can be the same or different, and R represents a $CH_3$ radical or $CF_3$ radical, provided that no substituent $R^1$ is present at Z if X—Y-Z represents the group $CH_2$—C=C, $R^6$ is a hydrogen atom or can also have the meanings that are indicated under $R^7$, $R^7$ stands for R or P-Q-R bonded via P to the basic ring structure, whereby these groups have the above-mentioned meanings, $R^{11}$ represents a halogen, $R^{13}$ is a methyl or ethyl group, and $R^{17}$ is hydrogen or stands for C(O)—$R^{18}$, whereby $R^{18}$ is a straight-chain or branched-chain $C_1$ to $C_{18}$ alkyl, -alkenyl, -alkinyl radical or an aryl radical, or stands for T-U—V bonded via T to the C(O) group, whereby T and U represent straight-chain or branched-chain $C_1$ to $C_{18}$ alkylene, -alkenylene, -alkinylene groups, alicyclic $C_3$ to $C_{12}$ groups or aryl groups and are the same or different, and V is a straight-chain or branched-chain $C_1$ to $C_{18}$ alkyl, -alkenyl or -alkinyl radical or an aryl radical, or $R^{18}$ has one of the above-mentioned meanings and in addition is substituted with one or more groups $NR^{19}R^{20}$ or one or more groups $SO_xR^{21}$, whereby x=0, 1 or 2, and $R^{19}$, $R^{20}$ and $R^{21}$ in each case are hydrogen or T-U—V bonded via T to N, S with the above-mentioned meaning, provided that in addition, the physiologically compatible addition salts with inorganic and organic acids are included. The $R^{11}$ group is preferably fluorine.

As an alternative, in this case, it can also be chlorine, bromine or iodine, however.

In particular, the $R^6$ group can be hydrogen, methyl, ethyl or fluoromethyl. $R^6$ preferably stands for hydrogen.

In particular, the $R^7$ group can be methyl, ethyl or fluoromethyl. $R^7$ is preferably methyl.

It is especially advantageous if $R^1$ is hydrogen, so that this is a 19-nortestosterone derivative. Basically, however, $R^1$ can also be methyl, ethyl, propyl or butyl or a fluorinated, especially perfluorinated derivative of these radicals.

$R^{13}$ can be methyl or ethyl. In particular, $R^{13}$ is methyl.

$R^{17}$ is preferably hydrogen or C(O)—$R^{18}$, whereby $R^{17}$ is a straight-chain or branched-chain alkyl radical.

If substituent $R^{18}$ in the grouping C(O)—$R^{18}$ for $R^{17}$ is an alkyl, in this connection this can be in particular methyl, ethyl, propyl, butyl, pentyl, hexyl, heptyl, octyl, nonyl, decyl, undecyl, dodecyl, tridecyl, tetradecyl, pentadecyl, hexadecyl, heptadecyl and octadecyl, whereby both the unbranched and the branched derivatives, thus in particular isopropyl, isobutyl, tert-butyl, isopentyl, tert-pentyl and neopentyl, are suitable. Within the aforementioned alkyl residues hexyl, heptyl, octyl, nonyl and decyl are especially preferred.

If $R^{18}$ is an alkenyl, this can be in particular ethenyl as well as 1- or 2-propenyl. If $R^{18}$ is alkinyl, this can be in particular ethinyl as well as 1- or 2-propinyl.

If $R^{18}$ is represented by grouping T-U—V, in this case this can be in first line methylenecyclohexyl that is bonded via the methylene group to the CO group or ethylene cyclohexyl that is bonded via the ethylene group in 1- or 2-position to the CO group.

The upper limit of carbon atoms in the straight of P-Q-R and T-U—V shall be 22.

As aryl radicals in the C(O)—$R^{18}$ substituent, in particular phenyl and 1-naphthyl or 2-naphthyl can be suitable. In the same manner, aralkyl radicals T-U—V can be in particular benzyl, phenylethyl, phenylpropyl, naphthylmethyl and naphthylethyl.

Aryl in the C(O)—$R^{18}$ substituent can likewise mean heteroaryl. Examples of heteroaryl radicals are in particular 2-, 3- and 4-pyridinyl, 2- and 3-furyl, 2- and 3-thienyl, 2- and 3-pyrrolyl, 2-, 4- and 5-imidazolyl, pyridazinyl, 2-, 4- and 5-pyrimidinyl as well as 2- and 4-pyridazinyl.

If $R^{18}$ in addition is substituted with a group $NR^{19}R^{20}$, in this connection this can be a methylamino, dimethylamino, ethylamino, diethylamino, cyclohexylamino, dicyclohexylamino, phenylamino, diphenylamino, benzylamino or dibenzylamino group. In this case, the corresponding physiologically compatible addition salts with inorganic and organic acids are also included. As physiologically compatible addition salts with inorganic acids, in particular the hydrochlorides, hydrobromides, acetates, citrates, oxalates, tartrates and methanesulfonates are suitable.

In particular, the following 11β-halogen steroids are preferred:

11β-Fluoro-17β-hydroxy-7α-methyl-estr-4-en-3-one,
11β-Chloro-17β-hydroxy-7α-methyl-estr-4-en-3-one,
11β-Bromo-17β-hydroxy-7α-methyl-estr-4-en-3-one,
17β-Hydroxy-11β-iodo-7α-methyl-estr-4-en-3-one,
7α-Ethyl-11β-fluoro-17β-hydroxy-estr-4-en-3-one,
11β-Fluoro-7α-(fluoromethyl)-17β-hydroxy-estr-4-en-3-one,
11β-Fluoro-17β-heptanoyloxy-7α-methyl-estr-4-en-3-one,
11β-Fluoro-7α-methyl-17β-undecanoyloxy-estr-4-ene-3-one,
11β-Fluoro-17β-hydroxy-7α-methyl-estr-5(10)-en-3-one.

The above-mentioned 11β-halogen steroids with general formula I are especially suitable for the production of pharmaceutical agents.

In addition, the invention relates to pharmaceutical preparations that contain at least one pharmaceutically compatible vehicle in addition to at least one of the above-mentioned 11β-halogen steroids.

The 11β-halogen steroids of general formula I according to the invention are compounds with strong androgenic action without the above-mentioned side effects as for instance stimulation of the prostate (in particular no benign prostate hyperplasia). They can be easily synthesized. It has been shown that the 11β-halogen steroids can be used not only for male HRT but are also suitable without additional administration of additional active ingredients as effective male contraceptive agents if a sufficient dosage is made to drop the blood level of LH, of testosterone that is produced in the body as well as FSH (follicle stimulating hormone) sufficiently. This depends on the 11β-halogen steroids according to the invention inhibiting the release of LH and FSH. LH stimulates the Leydig cells, so that testosterone is secreted. If the blood level of the LH is kept low, the endogenous testosterone release also drops. Testosterone is required for spermatogenesis, while FSH stimulates the germ cells. Sufficiently high FSH and LH blood levels are therefore necessary for an effective spermatogenesis, whereby a sufficiently high LH blood level results in the testosterone release that is necessary for spermatogenesis.

Since treatment with just the 11β-halogen steroids without additional active ingredients for sterilization can provide for effective male contraception, the administration of a pharmaceutical agent that is suitable for this purpose can be significantly simplified, and the costs of the treatment are considerably decreased.

The 11β-halogen steroids of this invention can also be used in combination with a progestogen to control male fertility.

Moreover, the 11β-halogen steroids according to the invention effectively inhibit 5α-reductase and the steroid-11-hydroxylase [CYP11B (P450c11), G. Zhang, W. L. Miller, Journal of Clinical Endocrinology and Metabolism, Vol. 81, pages 3254-3256 (1996)], so that, for example, the stimulation of the prostate is avoided in a selective manner, and these compounds exhibit improved pharmacokinetics. The inhibition of the 11-hydroxylase results in a reduced deactivation of the androgenic compounds and in their reduced excretion from the human body. As a result, the effectiveness and the duration of action of these compounds compared to known compounds are improved especially after oral administration.

For the reasons above, these compounds are especially suitable for use in male birth control as well as for androgen replacement therapy with a reduced tendency toward 5α-reduction with simultaneously obtained aromatizability to form estrogenic steroids and advantageous influence on serum lipids and the central nervous system.

The androgenic action and the observation that the above-mentioned side effects do not occur were determined "in vivo" in rats:

Anabolic and Androgenic Activity in the Juvenile Male Rat

The test by Hershberger et al. (1953) is used as a screening test method for detecting androgenic properties:

Principle. The function and size of the accessory reproductive glands (seminal vesicles, prostate) and of the muscle (e.g. M. levator ani) are androgen dependent. Castration leads to the atrophy of these organs, the substitution with androgenic compounds stimulates growth and function in a dose dependent manner.

Test description. In the juvenile male castrated rat, pharmacologically active agonists of androgens stimulate the growth of the prostate, seminal vesicles (androgenic property) and Musculus levator ani (anabolic property). The treatment for seven days of juvenile castrated male rats with daily administration of compound A: 11β-Fluoro-17β-hydroxy-7α-methyl-estr-4-en-3-one,(different doses), compound B: 7α-methyl-19-nortestosterone (different doses), testosterone propionate (reference) and benzylbenzoate/ricinus oil (solvent and control), respectively, was used to determine the androgenic and anabolic potency of eF-MENT. Analyses: relative weights of prostate, seminal vesicles and M. levator ani.

(Hershberger, L G, Shipley, E G, Meyer, R K (1953). Myotrophic activity of 19-nortestosterone and other steroids determined by modified levator ani muscle method. Proc. Soc. Exp. Biol. Med. 83: 175-180.)

Comparison of Compound A: 11β-Fluoro-17β-hydroxy-7α-methyl-estr-4-en-3-one, and compound B: 7α-methyl-19-nortestosterone Prostate:

| Dose mg * kg$^{-1}$ * Day$^{-1}$ | Compound A rel. Weight [mg/100 g] | Stimulation [mean] | Compound B rel. Weight [mg/100 g] | Stimulation [mean] |
|---|---|---|---|---|
| 0.005 | | | 8.9 | 4.3 |
| 0.015 | 19.7/18.5 | 30.0 | 14.6/20.0 | 24.0 |
| 0.03 | 25.2 | 40.1 | | |
| 0.05 | 34.1 | 76.6 | 24.7/31.7 | 51.3 |
| 0.15 | 44.9/47.5/41.7 | 93.8 | 40.6 | 90.2 |
| 0.3 | 59.5 | 125.1 | | |
| 1.5 | 64.6 | 137.3 | | |

Animals: ORX, juvenile rats, duration of treatment: 7 days.

Seminal Vesicles:

| Dose mg * kg$^{-1}$ * Day$^{-1}$ | Compound A rel. Gewicht [mg/100 g] | Stimulation [mean] | Compound B rel. Gewicht [mg/100 g] | Stimulation [mean] |
|---|---|---|---|---|
| 0.005 | | | 9.2 | 4.6 |
| 0.015 | 18.6/15.5 | 18.6 | 13.6/19.2 | 17.0 |

-continued

| Dose mg * kg$^{-1}$ * Day$^{-1}$ | Compound A rel. Gewicht [mg/100 g] | Stimulation [mean] | Compound B rel. Gewicht [mg/100 g] | Stimulation [mean] |
|---|---|---|---|---|
| 0.03 | 26.8 | 35.6 | | |
| 0.05 | 43.6 | 59.2 | 36.8/39.0 | 51.8 |
| 0.15 | 57.9/64.4/ 49.3 | 85.5 | 65.5 | 87.8 |
| 0.3 | 93.4 | 144.8 | | |
| 1.5 | 120.0 | 189.3 | | |

Animals: ORX, juvenile rats, duration of treatment: 7 days.

M. Levator Ani

| Dose mg * kg$^{-1}$ * Day$^{-1}$ | Compound A rel. Weight [mg/100 g] | Stimulation [mean] | Compound B rel. Weight [mg/100 g] | Stimulation [mean] |
|---|---|---|---|---|
| 0.005 | | | 36.6 | 71.3 |
| 0.015 | 54.9/50.8 | 79.5 | 38.1/53.7 | 92.6 |
| 0.03 | 56.5 | 93.3 | | |
| 0.05 | 59.4 | 118.0 | 48.1/59.4 | 150.7 |
| 0.15 | 64.7/63.67 1.7 | 154.5 | 59.4 | 283.4 |
| 0.3 | 69.8 | 180.4 | | |
| 1.5 | 69.9 | 181.0 | | |

Animals: ORX, juvenile rats, duration of treatment: 7 days.

In these tests the compound A as one representative of the compounds according to the invention shows an activity profile comparable to the prior art compound B demonstrating that the compounds of the invention can be used analogously to the known compounds.

Stability in Liver Microsomes

The metabolic stability of the compounds has been tested in liver microsomes of various species (commercially available). It is possible to make predictions as to the first-pass-metabolism in human by using human test material. A rapid degradation of the test material gives hints at low oral bio-availability of the substance tested.

Isolated microsomes from various species are incubated in the presence of at least two concentrations of the test compounds for two different periods of time at comparable metabolic activity (cytochrome P 450 enzymes). The points in time correspond with the ones in which degradation of reference compounds can be demonstrated. The amount of the remaining compound is quantified by comparison with the amount remaining after 0 mins.

In the corresponding configuration, references to phase-I metabolites and to the CYP isoenzymes that are involved can be obtained. If liver microsomes are supplemented with additives, glucuronidations (phase-II reaction) can also be observed in addition to phase-I reactions.

Species Specific Stability of Test Compounds in Liver at a Concentration of 3 μM

| | Compound B (%) left unchanged | | Compound A (%) left unchanged | |
|---|---|---|---|---|
| Species | after 30 min | after 60 min | after 30 min | after 60 min |
| Human | 37 | 19 | 59 | 41 |
| Mouse | 4 | 4 | 20 | 11 |
| Rat | 4 | 6 | 5 | 7 |

The metabolic stability of compound A representing compounds according to this invention has proved higher than that of compounds of the prior art.

The compounds according to the invention or the pharmaceutical preparations according to the invention that contain these compounds are extremely well suited for treating non-sterile male patients as well as basically also male mammals. A treatment for contraception results in that the male patients to be treated are only temporarily sterile. After the treatment with the active ingredients according to the invention or the pharmaceutical preparations is completed, the original state is produced again, so that the previously treated male patient is no longer sterile, and the spermatogenesis takes place again to the original extent. To keep the condition of temporary sterility constant over a desired period, the administration of the active ingredient or the preparation is to be performed continuously, whereby the administration, depending on the form of administration, is to be repeated either daily, at a shorter interval or else periodically at a longer interval. After the one-time or repeated administration of the active ingredient or the preparation is completed, the non-sterile condition of the male patient optionally is not immediately restored but rather only slowly restored, whereby the time span that is necessary for this purpose depends on various factors, for example the dosage, the body constitution of the treated patients and the parallel administration of other pharmaceutical agents.

If the purpose of treatment in the contraception exists, the dosage of the 11β-halogen steroids must be set high so that the blood levels of LH and FSH in each case are at most 2.5 I.E./ml (I.E.: International Units), especially at most 1.0 I.E./ml, and the blood level of testosterone is at most 10 nmol/l, especially at most 3 nmol/l.

If the compounds according to the invention are to be used for HRT without a contraception being achieved, the dosage is set lower. For this case, an attempt is made to achieve effect levels that make possible the blood levels for LH and FSH of respectively more than 2.5 I.E./ml and for testosterone of more than 10 nmol/l.

The dosages of the 11β-halogen steroids according to the invention that are required to set the blood level of LH, FSH and testosterone depend on a number of factors and must therefore be determined in an application-specific manner. First, the dosage is naturally dependent on the type of therapy. If the compounds for male contraception are to be used, significantly higher doses must be given than in the case of a use for HRT. The dosage also depends on the type of 11β-halogen steroid and its bio-availability. The type of use is also essential for the amount to be administered. Finally, the dosage also depends on the body constitution of the patient to be treated and other factors, for example the state of whether other pharmaceutical agents are provided in parallel.

The compounds can be administered orally and parenterally, for example i.p. (intraperitoneally), i.v. (intravenously), i.m. (intramuscularly) or percutaneously. The compounds can also be implanted in the tissue. The amount of the compounds to be administered can fluctuate within a wide range if an effective amount is administered. Based on the condition to be treated or based on the effect to be achieved and the type of dispensing, the amount of administered compound can vary within a wide range. In humans, the daily dose is in the range of 0.1 to 100 mg. The preferred daily dosage in humans is 0.1 to 10 mg. The duration of treatment depends on the purpose to be achieved.

Capsules, pills, tablets, coated tablets, creams, ointments, lotions, liquids, such as syrups, gels, injectable liquids, for example for i.p., i.v., i.m. or percutaneous injection, etc., are suitable for use, whereby the individual forms for dispensing release the compounds according to the invention to the body gradually or in the entire amount within a short time depending on the type thereof.

For oral administration, capsules, pills, tablets, coated tablets and liquids or other known oral forms for dispensing are used as pharmaceutical preparations. In this case, the pharmaceutical agents can be formulated in such a way that they release the active ingredients either in a short time and deliver them to the body or they have a depot action, so that a prolonged, slow feed of active ingredient to the body is achieved. In addition to the 11β-halogen steroid, the dosage units can contain one or more pharmaceutically compatible vehicles, for example substances for adjusting the rheology of the pharmaceutical agent, surfactants, solubilizers, microcapsules, microparticles, granulates, diluents, binders, such as starch, sugar, sorbitol and gelatin, also fillers, such as silicic acid and talc, lubricants, dyes, perfumes and other substances.

In particular, the 11β-halogen steroids according to the invention can also be formulated in the form of a solution that is intended for oral administration and that in addition to the active 11β-halogen steroid contains as the following components: a pharmaceutically compatible oil and/or a pharmaceutically compatible lipophilic surfactant and/or a pharmaceutically compatible hydrophilic surfactant and/or a pharmaceutically compatible water-miscible solvent. In this respect, reference is also made to WO-A-97/21440.

To achieve better bio-availability of the steroid, the compounds can also be formulated as cyclodextrin clathrates. For this purpose, the compounds are reacted with α-, β- or γ-cyclodextrin or derivatives thereof (PCT/EP95/02656).

If creams, ointments, lotions and liquids that can be applied topically are to be used, the latter must be constituted in such a way that the compounds according to the invention are fed to the body in a sufficient amount. In these forms for dispensing, adjuvants are contained, for example substances for adjusting the rheology of pharmaceutical agents, surfactants, preservatives, solubilizers, diluents, substances for increasing the permeability of the steroids according to the invention through the skin, dyes, perfumes and skin protection agents, such as conditioners and moisturizers. Together with the steroids according to the invention, other active ingredients can also be contained in the pharmaceutical agent.

For parenteral administration, the active ingredients can be dissolved or suspended in a physiologically compatible diluent. As diluents, very often oils with or without the addition of a solubilizer, a surfactant, a suspending agent or emulsifier are used. Examples of oils that are used are olive oil, peanut oil, cottonseed oil, soybean oil, castor oil and sesame oil. To formulate an injectable preparation, any liquid vehicle can be used in which the compounds according to the invention are dissolved or emulsified. These liquids frequently also contain substances to regulate viscosity, surfactants, preservatives, solubilizers, diluents and other additives, with which the solution is set to isotonic. Other active ingredients can also be administered together with the 11β-halogen steroids.

The 11β-halogen steroids can be administered in the form of a depot injection or an implant preparation, for example subcutaneously, which can be formulated in such a way that a delayed release of active ingredients is made possible. To this end, known techniques can be used, for example depots that dissolve or that operate with a membrane. Implants can contain as inert materials, for example, biodegradable polymers or synthetic silicones, for example silicone gum. The 11β-halogen steroids can also be incorporated in, for example, a patch, for percutaneous administration.

There are various methods for synthesis of the 11β-halogen steroids according to the invention. Below, two of these methods are shown by way of example:

Starting from a compound with general formula B, D

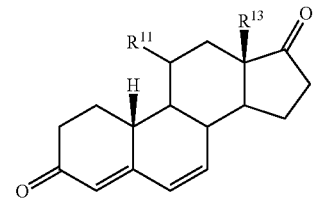

B, D whereby $R^{11}$ can represent either a hydroxyl group, a halogen or a nucleophilic leaving group, and $R^{13}$ has the above-indicated meaning, a compound with general formula B', E is first formed by 1,6-addition of a metallated alkyl with general formula $R^7$-M or $R^7$-M'X, whereby M is an alkali metal, M' is an alkaline-earth metal, X is a halogen atom, and $R^7$ has the above-mentioned meaning:

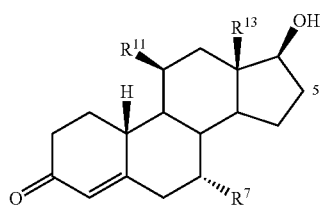

B', E and this compound then is reduced either selectively to a compound with general formula I or, if $R^{11}$ is not halogen, is nucleophilically substituted in 11-position with a halogenating agent and then is reduced selectively to the compound with general formula I:

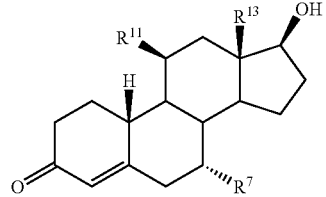

For synthesis, the process starts from a first embodiment of compound A, for example 11β-hydroxy-19-norandrost-4-ene-3,17-dione (J. de Flines et al., Recl. Trav. Chim. Pays-Bas, Vol. 82, pages 129 ff. (1963)):

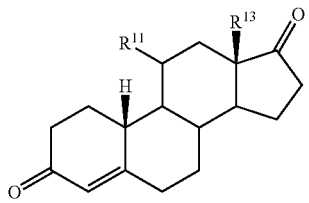

For 11α-hydroxy-19-norandrost-4-ene-3,17-dione, $R^{11}$=OH and $R^{13}$=methyl.

Compound A (with $R^{11}$=OH) is reacted in a first reaction with a halodehydroxylating reagent, for example hydrofluoric acid, hydrochloric acid, hydrobromic acid or hydroiodic acid, thionyl chloride or thionyl bromide, phosphorus pentachloride, phosphorus oxychloride, N-chlorosuccinimide, triphenylphosphine/carbon tetrachloride, HF/pyridine or diethylaminosulfur trifluoride or preferably nonaflyl fluoride/1,5-diazabicyclo[5.4.0]undecene to form halo-norandrostenedione. The 11β-halogen-norandrost-4-ene-3,17-dione is formed according to general formula A' above ($R^{11}$=halogen).

Then, a $\Delta^6$-double bond is introduced, for example by the 3-keto-$\Delta^4$ system first being converted under proton catalysis into the 3,5-dien-3-ol-ether A":

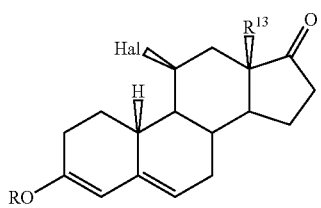

whereby Hal=F, Cl, Br, I and compound A" then is converted, for example, by bromination/dehydrobromination, especially with N-bromosuccinimide or 1,3-dibromo-5,5-dimethylhydantoin and pyridine treatment or lithium bromide/lithium carbonate treatment, into the $\Delta^{4,6}$-ketone with general formula B.

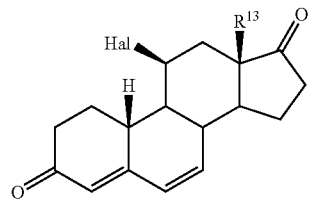

By copper-catalyzed 1,6-addition of a metallated alkyl, for example methylmagnesium bromide or methyllithium, B is then alkylated in 7-position to compound B':

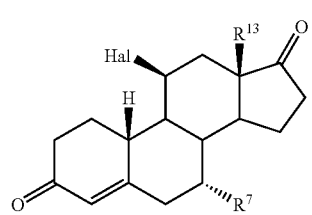

In the next step, the 7α-alkyl-11β-halogen-norandrost-4-ene-3,17-dione B' that is produced is treated at low temperatures, for example in THF or diethyl ether with sodium borohydride, whereby the 17-ketone is reduced selectively. In this case, 7α-alkyl-11β-halogen-17β-hydroxy-norandrost-4-en-3-one I according to the invention is produced:

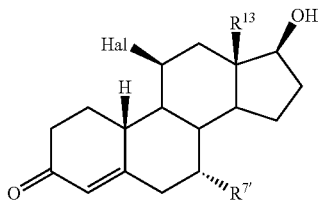

The hydroxy group is then optionally esterified in 17-position with acyl anhydrides or acyl chlorides, for example with acetyl chloride, butanoyl chloride or enantoyl chloride, in the presence of suitable bases, such as, e.g., pyridine. In this case, the corresponding esters I' according to the invention are produced:

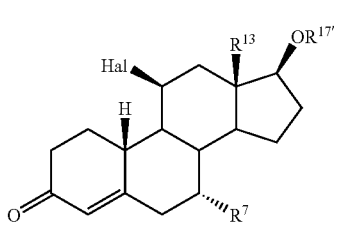

For the production of the alternative 11β-halogen steroids I", namely the 7α-alkyl-11β-halogen-17β-hydroxy-norandrost-5(10)-en-3-ones, the $\Delta^4$-3-ketone group of compound I is first ketalized, whereby mixtures of the Δ⁵- and the Δ⁵⁽¹⁰⁾-double-bond-isomeric ketals C are produced:

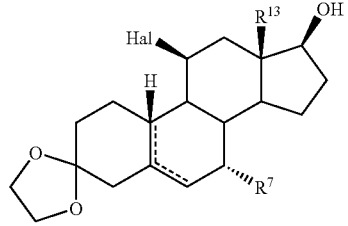

C

These mixtures are carefully deketalized, and the isomers are separated, whereby 7α-alkyl-11β-halogen-17β-hydroxy-norandrost-5(10)-en-3-ones I″ according to the invention are isolated:

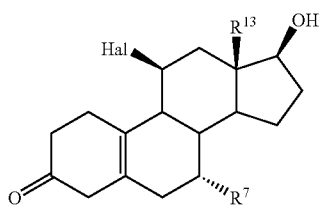

I″

In an alternative synthesis method, the compounds of formula I, starting from 11α-acetoxy-19-norandrosta-4,6-diene-3,17-dione D (CAS: 228570-21-6):

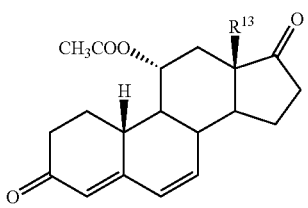

D whereby R¹³=methyl, can be reacted by copper-catalyzed 1,6-addition of a metal alkyl, such as, e.g., methylmagnesium bromide or methyllithium, for example in THF or diethyl ether, at low temperatures to form compounds with general formula E:

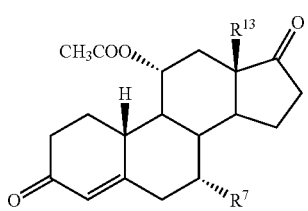

E

Then, compounds E are saponified, for example with a methanolic KOH solution, whereby 11β-hydroxy derivatives F are produced:

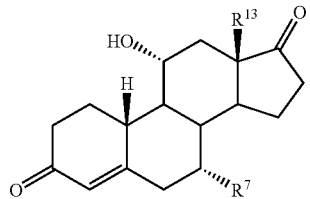

F

The latter are then reacted with halodehydroxylating reagents, for example hydrofluoric acid, hydrochloric acid, hydrobromic acid or hydroiodic acid, thionyl chloride or thionyl bromide, phosphorus pentachloride, phosphorous oxychloride, N-chlorosuccinimide, triphenylphosphine/carbon tetrachloride, HF/pyridine or diethylaminosulfur trifluoride or preferably nonaflyl chloride/1,5-diazabicyclo[5.4.0] undecene to form 7α-alkyl-11β-halogen-17β-hydroxyandrost-4-ene-3,17-dione, which then is reduced at low temperatures, for example in THF or diethyl ether, selectively with sodium borohydride in 17-position to 7α-alkyl-11β-halogen-17β-hydroxy-androst-4-en-3-one I.

The invention is explained in more detail with the examples below:

EXAMPLE 1

Figure 1:
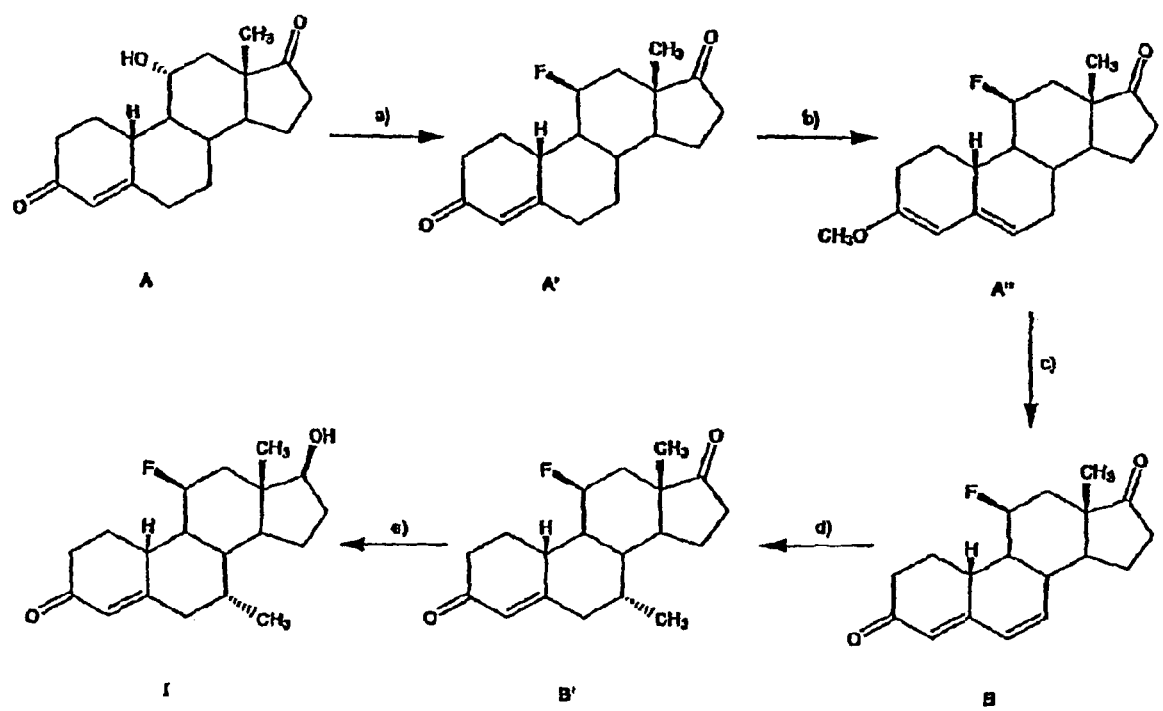
FIG. 1. Illustrates a synthesis scheme for the production of 11β-Fluoro-17β-hydroxy-7α-methylestr-4-en-3-one (I).

Production of 11β-Fluoro-17β-hydroxy-7α-methyl-estr-4-en-3-one (I) (Diagram A, FIG. 1)

a) 11β-Fluoro-estr-4-ene-3,17-dione (A'):

4.6 ml of perfluorobutane-1-sulfonic acid fluoride was added in drops at 0° C. to 5.0 g of 11β-hydroxy-estr-4-ene-3,17-dione (A) [J. de Flines et al., Recl. Trav. Chim. Pays-Bas, Vol. 82, pages 129 ff., (1963)) in 100 ml of toluene and 7.3 ml of 1,8-diazabicyclo[5.4.0]undec-7-ene. After 30 minutes, the solution was diluted with ethyl acetate, washed with saturated sodium chloride solution and dried. Then, it was concentrated by evaporation in a vacuum. After the crude product was chromatographed on silica gel with a hexane-ethyl acetate gradient, 3.8 g of 11β-fluoro-estr-4-ene-3,17-dione (A') with a melting point of 173-174° C. was obtained.

b) 11β-Fluoro-3-methoxy-estra-3,5-dien-17-one (A″):

7.8 g of 11β-fluoro-estr-4-ene-3,17-dione (A') was stirred in 40 ml of 2,2-dimethoxypropane with 780 mg of pyridinium-toluene-4-sulfonate for 5 hours at 80° C. Then, 1.5 ml of triethylamine was added. Then, it was diluted with ethyl acetate and washed with saturated sodium chloride solution. After crystallization from methanol, 5.3 g of 11β- fluoro-3-methoxy-estra-3,5-dien-17-one (A") with a melting point of 173° C. was obtained.

c) 11β-Fluoro-estra-4,6-diene-3,17-dione (B):

5 ml of a 10% by weight sodium acetate solution and, in portions, 2.5 g of 1,3-dibromo-5,5-dimethylhydantoin were added in succession at 0° C. to 5.0 g of 11β-fluoro-3-methoxy-estra-3,5-dien-17-one (A") in 50 ml of DMF. After 30 minutes, 2.3 g of sodium sulfite and then 2.5 g of lithium bromide and 2.0 g of lithium carbonate were added and stirred for 2 hours at 100° C. The reaction mixture was stirred into ice water. The precipitated product was suctioned off, dissolved in ethyl acetate, washed with water, dried and concentrated by evaporation in a vacuum. After recrystallization from ethyl acetate, 3.6 g of 11β-fluoro-estra-4,6-diene-3,17-dione (B) with a melting point of 198° C. was obtained.

d) 11β-Fluoro-7α-methylestr-4-ene-3,17-dione (B'):

68.7 mg of copper(I) chloride was added at room temperature to a solution of 2 g of 11β-fluoro-estra-4,6-diene-3,17-dione (B) in 36 ml of tetrahydrofuran. The solution was then stirred for 10 minutes, before the reaction mixture was cooled to −15° C. Then, it was mixed with 427 mg of aluminum chloride, stirred for 30 minutes at this temperature, mixed drop by drop with 4.63 ml of methylmagnesium bromide solution and stirred for another 5 hours at −10° C.

For working-up, the reaction mixture was mixed at −10° C. with 4N hydrochloric acid, stirred for 1.5 hours at room temperature, added to water, extracted three times with ethyl acetate, dried on sodium sulfate, concentrated by evaporation in a vacuum and chromatographed on silica gel with hexane/ethyl acetate. 1.0 g of pure 11β-fluoro-7α-methyl-estr-4-ene-3,17-dione (B') with a melting point of 101.4° C. was obtained ($[\alpha]_D^{20}$=+135.8° (c=0.525% in chloroform)). From a later fraction, 0.17 g of the isomeric 11β-fluoro-7β-methylestr-4-ene-3,17-dione with a melting point of 84.8° C. was obtained ($[\alpha]_D^{20}$=+93.7° (c=0.525% in chloroform)).

e) 11β-Fluoro-17β-hydroxy-7α-methylestr-4-ene-3-one (I):

A solution of 500 mg of 11β-fluoro-7α-methylestr-4-ene-3,17-dione (B') in 10 ml of tetrahydrofuran, 5.8 ml of ethanol and 1.15 ml of water was stirred at −55° C. with 175.6 mg of sodium borohydride for 2.5 hours. After another 351.2 mg of sodium borohydride was added, it was stirred for another 1.5 hours at −55° C., then added to ice water, extracted three times with ethyl acetate, washed neutral, dried on sodium sulfate and concentrated by evaporation in a vacuum. Then, it was chromatographed on silica gel with hexane/ethyl acetate. 230 mg of pure 11β-fluoro-17β-hydroxy-7α-methylestr-4-ene-3-one (I) with a melting point of 126.7° C. was obtained ($[\alpha]_D^{20}$=+79.9° (c=0.53% in chloroform)).

The synthesis above can also be modified to introduce higher homologs of the 7α-methyl group and derivatives thereof into the steroid skeleton by the corresponding alkylmagnesium bromide solution being used in synthesis step d) instead of methylmagnesium bromide solution or the corresponding derivatives thereof. Thus, for example, 7α-ethyl-11β-fluoro-17β-hydroxy-estr-4-ene-3-one and 11β-fluoro-7α-(fluoromethyl)-17β-hydroxy-estr-4-ene-3-one can also be produced.

EXAMPLE 2

Figure 2:
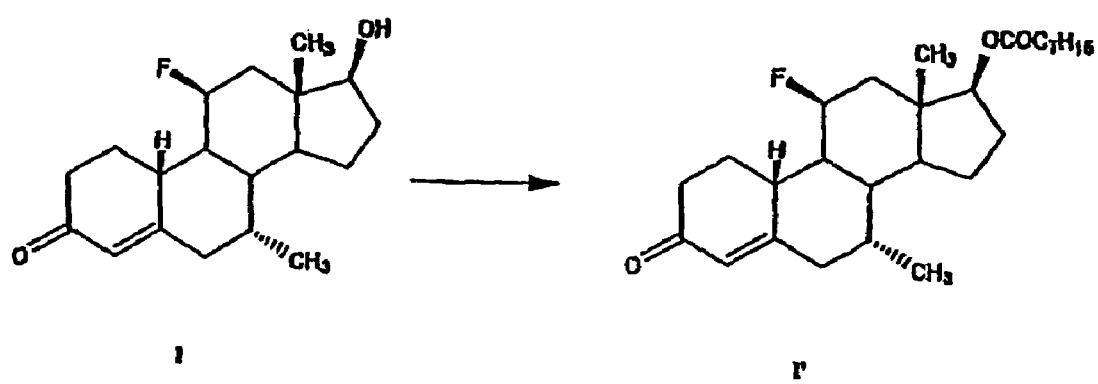
FIG. 2. Illustrates a synthesis scheme for the production of 11β-Fluoro-17β-heptanoyloxy-7α-methylestr-4-en-3-one (I').

Production of 11β-Fluoro-17β-heptanoyloxy-7α-methylestr-4-en-3-one (I') (Diagram B, FIG. 2)

A solution of 220 mg of 11β-fluoro-17β-hydroxy-7α-methylestr-4-ene-3-one (I) in 5 ml of tetrahydrofuran and 1.09 ml of pyridine was mixed drop by drop at 0° C. with 1.09 ml of heptanoyl chloride and stirred for 1 hour. Then, it was mixed with sodium bicarbonate solution, extracted three times with ethyl acetate, washed neutral, dried on sodium sulfate, concentrated by evaporation in a vacuum and chromatographed on silica gel with hexane/ethyl acetate. 210 mg of pure 11β-fluoro-17β-heptanoyloxy-7α-methylestr-4-en-3-one (I') was obtained as a foam ($[\alpha]_D^{20}$=+40.8° (c=0.56% in chloroform)).

The synthesis above can also be modified to introduce higher homologs of the 17β-heptanoyl group by the corresponding alkanoyl chloride being used instead of heptanoyl chloride. Thus, for example, 11β-fluoro-7α-methyl-17β-undecanoyloxy-estr-4-en 3-one can also be produced.

EXAMPLE 3

Figure 3:
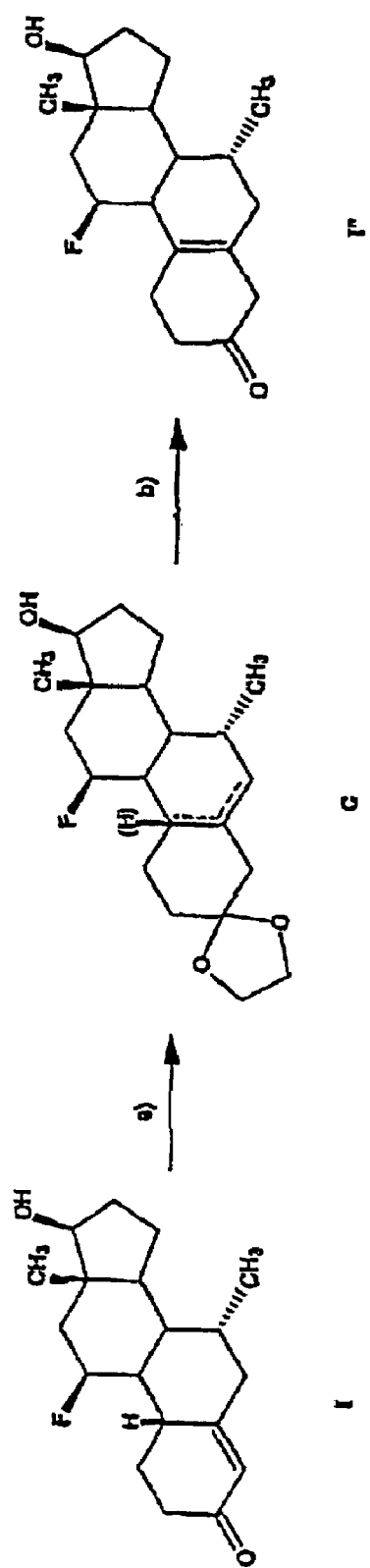
FIG. 3. Illustrates a synthesis scheme for the production of 11β-Fluoro-17β-hydroxy-7α-methylestr-5(10)-en-3-one (I″).

Production of 11β-Fluoro-17β-hydroxy-7α-methyl-estr-5(10)-en-3-one (I") (Diagram C, FIG. 3)

a) 3-Ethylenedioxy-11β-fluoro-7α-methylestr-5(10)-en-17β-ol (C):

3.63 ml of ethylene glycol and 1.82 ml of trimethyl orthoformate and 23.6 ml of para-toluenesulfonic acid hydrate were added to a solution of 500 mg of 11β-fluoro-17β-hydroxy-7α-methyl-estr-4-en-3-one (I) in 6.35 ml of dichloromethane. The reaction mixture was stirred for 20 hours at room temperature. Then, it was mixed with sodium carbonate solution, diluted with ethyl acetate, washed neutral, dried on sodium sulfate, concentrated by evaporation in a vacuum and chromatographed on silica gel with hexane/ethyl acetate. 170 mg of 3-ethylenedioxy-11β-fluoro-7α-methylestr-5(10)-en-17β-ol (C), which contained portions of double-bond-isomeric 3-ethylenedioxy-11β-fluoro-7α-methylestr-5-en-17β-ol (C), was obtained.

b) 11β-Fluoro-17β-hydroxy-7α-methyl-estr-5(10)-en-3-one (I"):

A solution of 170 mg of product (C), obtained under 3a), in 22.5 ml of methanol was stirred with 300 mg of oxalic acid and 3 ml of water for 24 hours at room temperature. Then, it was mixed with sodium bicarbonate solution, extracted three times with ethyl acetate, washed neutral, dried on sodium sulfate, concentrated by evaporation in a vacuum and chromatographed on silica gel with hexane/ethyl acetate. 62.7 mg of pure 11β-fluoro-17β-hydroxy-7α-methyl-estr-5(10)-en-3-one (I") was obtained. Crystallization from hexane yielded 47.6 mg of compound I" with a melting point of 169.9° C. ($[\alpha]_D^{20}$=+134.4° (c=0.56% chloroform)).

EXAMPLE 4

Figure 4:
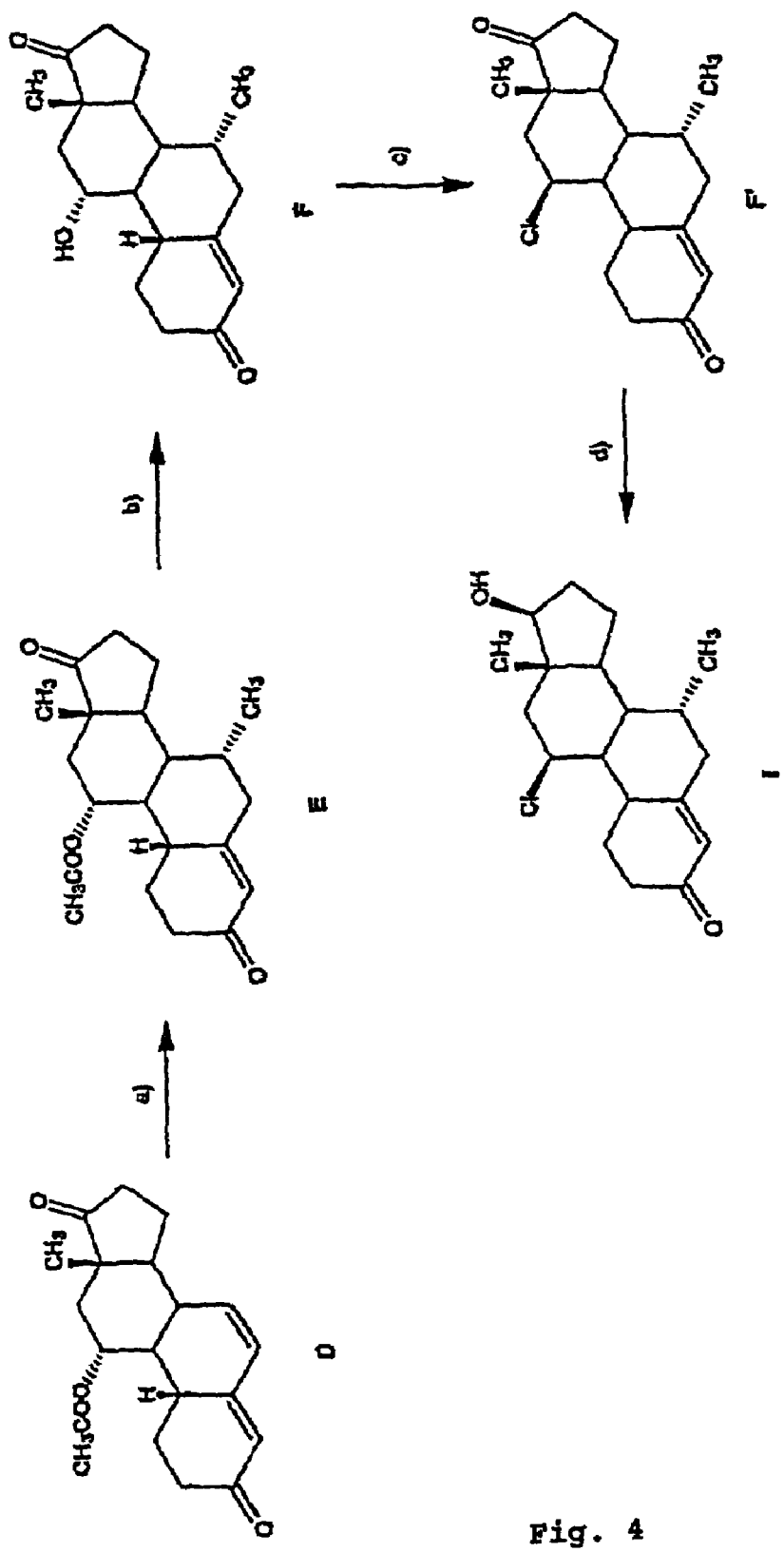
FIG. 4. Illustrates a synthesis scheme for the production of 11β-Chloro-17β-hydroxy-7α-methyl-estr-4-en-3-one (I).

Production of 11β-Chloro-17β-hydroxy-7α-methyl-estr-4-en-3-one (I) (Diagram D, FIG. 4)

a) 11α-Acetoxy-7α-methyl-estr-4-ene-3,17-dione (E):

A solution of 20 g of 11α-acetoxy-estra-4,6-diene-3,17-dione (D) in 500 ml of tetrahydrofuran, 20 ml of 1,3- dimethyl-3,4,5,6-tetrahydro-2(1H)-pyrimidinone and 20 ml of trimethylchlorosilane were added in drops within 1 hour at −30° C. in a prepared solution of 20 g of copper(I) iodide in 200 ml of tetrahydrofuran and 70 ml of methylmagnesium bromide. It was stirred for 1 hour at −20° C.

For working-up, the reaction mixture was then mixed at −20° C. with 20 ml of glacial acetic acid, stirred for 1 hour at room temperature, added to water, extracted three times with ethyl acetate, dried on sodium sulfate, concentrated by evaporation in a vacuum and chromatographed on silica gel with hexane/ethyl acetate. 12.8 g of pure 11α-acetoxy-7α-methylestr-4-ene-3,17-dione (E) with a melting point of 182.7° C. was obtained ($[\alpha]_D^{20}$=+24.7° (c=0.525% in chloroform)).

b) 11α-Hydroxy-7α-methyl-estr-4-ene-3,17-dione (F):

A solution of 1 g of 11α-acetoxy-7α-methyl-estr-4-ene-3,17-dione (E) in 20 ml of a 0.2 molar methanolic potassium hydroxide solution was stirred at room temperature for 3 hours. Then, it was added to water, extracted three times with ethyl acetate, washed neutral, dried on sodium sulfate, concentrated by evaporation in a vacuum and recrystallized from diethyl ether/acetone. 878 mg of pure 11α-hydroxy-7α-methyl-estr-4-ene-3,17-dione (F) with a melting point of 202.3° C. was obtained ($[\alpha]_D^{20}$=+44.8° (c=0.5% in chloroform)).

c) 11β-Chloro-7α-methyl-estr-4-ene-3,17-dione (F');

A solution of 800 mg of 11α-hydroxy-7α-methylestr-4-ene-3,17-dione (F) in 8 ml of dichloromethane was mixed at 0° C. with 1.21 ml of hexachloroacetone and 764 mg of triphenylphosphine and stirred at room temperature for 4 hours. Then, it was diluted with dichloromethane, washed neutral, dried on sodium sulfate, concentrated by evaporation in a vacuum and chromatographed on silica gel with hexane/ethyl acetate. 430 mg of pure 11β-chloro-7α-methyl-estr-4-ene-3,17-dione (F') with a melting point of 215.1° C. was obtained ($[\alpha]_D^{20}$=+182.7° (c=0.5% in chloroform)).

d) 11β-Chloro-17β-hydroxy-7α-methyl-estr-4-en-3-one (I):

A solution of 380 mg of 11β-chloro-7α-methyl-estr-4-ene-3,17-dione (F') in 7.6 ml of tetrahydrofuran, 4.4 ml of ethanol and 1.15 ml of water was mixed at −55° C. in portions with 596 mg of sodium borohydride and stirred for 7 hours at −55° C. Then, the mixture was added to ice water, extracted three times with ethyl acetate, washed neutral, dried on sodium sulfate, concentrated by evaporation in a vacuum and chromatographed on silica gel with hexane/ethyl acetate. 130 mg of pure 11β-chloro-17β-hydroxy-7α-methyl-estr-4-en-3-one (I) was obtained ($[\alpha]_D^{20}$=+136.9° (in chloroform), $F_D$183.2° C.).

The synthesis above can also be modified to produce the 11β-bromine and 11β-iodine derivatives, by a brominating or iodizing agent being used. Thus, for example, 11β-bromo-17β-hydroxy-7α-methyl-estr-4-en-3-one and 17β-hydroxy-11β-iodo-7α-methyl-estr-4-en-3-one can also be produced.

In analogy to Example 1 7α-Ethyl-11β-fluoro-17β-hydroxy-estr-4-en-3-one, using ethylmagnesium bromide instead of methylmagnesium bromide, is obtained; Fp. 115.1° C., $[\alpha]_D^{20}$=+62,1° (in chloroform). The intermediate 7α-Ethyl-11β-fluoro-estr-4-en-3,17-dione shows Fp.=174.9° C. and $[\alpha]_D^{20}$=+107,1° (chloroform).

Further compounds according to the invention are accesible by performing procedures in analogy to the mentioned prior art.

We claim:
1. An 11β-halogen steroid compound of formula I:

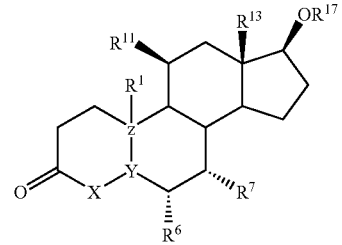

wherein
X—Y-Z is CH═C—C or CH$_2$—C═C
R$^1$ is either in α- or β-position, and is hydrogen, provided that no substituent R$^1$ is present at Z if X—Y-Z is CH$_2$—C═C,
R$^6$ is hydrogen atom or independently a group listed for R$^7$,
R$^7$ is R or P-Q-R bonded via P to the basic ring structure, wherein P and Q are each, independently of one another, a straight-chain or branched-chain C$_1$ to C$_8$ alkylene, -alkenylene, -alkynylene group which is optionally partially or completely fluorinated, and R is CH$_3$ or CF$_3$ radical,
R$^{11}$ is halogen,
R$^{13}$ is methyl or ethyl,
R$^{17}$ is hydrogen or C(O)—R$^{18}$, and
R$^{18}$ is a straight-chain or branched C$_1$ to C$_{18}$ alkyl, -alkenyl, or -alkynyl, or aryl radical, or T-U—V bonded via T to the C(O) group, wherein T and U are independently of one another, straight-chain or branched C$_1$ to C$_{18}$ alkylene, -alkenylene, or -alkynylene, C$_3$ to C$_{12}$ alicyclic group or aryl, and V is straight-chain or branched-C$_1$ to C$_{18}$ alkyl, -alkenyl or -alkynyl or an aryl; and said
R$^{18}$ is optionally substituted with one or more of NR$^{19}$R$^{20}$ or SO$_x$R$^{21}$, wherein x=0, 1 or 2, and R$^{19}$, R$^{20}$ and R$^{21}$ each independently is hydrogen or T-U-V bonded via T to N, or S,
or a physiologically compatible salt thereof.

2. A compound according to claim 1, wherein R$^{11}$ is fluorine.

3. A compound according to claim 2, wherein R$^6$ is hydrogen, methyl, ethyl or fluoromethyl.

4. A compound according to claim 2, wherein R$^7$ is methyl, ethyl or fluoromethyl.

5. A compound according to claim 2, wherein R$^1$ is hydrogen.

6. A compound according to claim 2, wherein R$^{13}$ is methyl.

7. A compound according to claim 2, wherein R$^{17}$ is hydrogen or C(O)—R$^{18}$, wherein R$^{18}$ is a straight-chain or branched C$_1$ to C$_{18}$ alkyl.

8. A compound according to claim 1, wherein R$^6$is hydrogen.

9. A compound according to claim 1, wherein R$^7$is methyl.

10. A compound according to claim 1, wherein R$^{17}$ is C(O)—R$^{18}$, wherein R$^{18}$ is a methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isopropyl, isobutyl, tert-butyl, isopentyl, tert-pentyl, neopentyl, ethenyl, 1-propenyl, 2-propenyl, 1-propinyl, 2-propinyl, 2-, 3- or 4-pyridinyl, 2- or 3-furyl, 2- or 3-thienyl, 2- or 3-pyrrolyl, 2-, 4- or 5-imidazolyl, pyridazinyl, 2-, 4- or 5-pyrimidinyl, or 2- or 4-pyridazinyl.

11. A compound according to claim 1, wherein $R^{17}$ is C(O)—$R_{18}$, wherein $R^{18}$ is methylenecyclohexyl that is bonded via the methylene group to the CO group or ethylene cyclohexyl that is bonded via the ethylene group in 1- or 2-position to the CO group.

12. A compound of claim 1 wherein X—Y-Z is $CH_2$—C=C.

13. A compound which is:
11β-Fluoro 17β-hydroxy-7α-methyl-estr-4-en-3-one,
11β-Chloro-17β-hydroxy-7α-methyl-estr-4-en-3-one,
11β-Bromo-17β-hydroxy-7α-methyl-estr-4-en-3-one,
17β-Hydroxy-11β-iodo-7α-methyl-estr-4-en-3-one,
7α-Ethyl-11β-fluoro-17β-hydroxy-estr-4-en-3-one,
11β-Fluoro-7α-(fluoromethyl)-17β-hydroxy-estr-4-en-3-one,
11β-Fluoro-17β-heptanoyloxy-7α-methyl-estr-4-en-3-one,
11β-Fluoro-17α-methyl-17β-undecanoyloxy-estr-4-ene-3-one, or
11β-Fluoro-17β-hydroxy-7α-methyl-estr-5(10)-en-3-one
or a physiologically compatible salt thereof.

14. A pharmaceutical composition comprising at least one compound according to claim 1 along with at least one pharmaceutically compatible vehicle.

15. A pharmaceutical composition comprising at least one compound according to claim 1 along with at least one pharmaceutically compatible vehicle and at least one progestogen.

16. A method for controlling male fertility and/or performing androgen replacement therapy in an animal comprising administering to said animal an effective amount of a compound of claim 1.

17. A method for controlling male fertility and/or performing androgen replacement therapy in an animal comprising administering to said animal an effective amount of a pharmaceutical composition of claim 10.

18. A method for controlling male fertility and/or performing androgen replacement therapy in an animal comprising administering to said animal an effective amount of a pharmaceutical composition of claim 11.

19. A method of modulating the activity of a 5α-reductase and steroid-11-hydroxylase [CYP11B(P450c11)] enzyme comprising contacting said enzyme with a compound of claim 1.

20. A process for the production of a compound of formula III comprising
(a) 1,6-addition of a metallated alkyl of formula $R^7$-M'X or $R^7$-M, wherein M is an alkali metal, M' is an alkaline-earth metal, X is a haloaen atom, and $R^7$ is as defined in claim 1, onto a compound of formula B, D

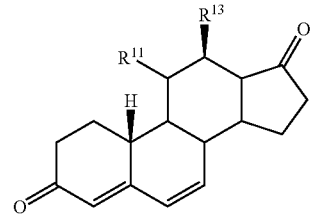

wherein $R^{11}$ is hydroxyl group, halogen or a nucleophilic leaving group, and $R^{13}$ is as defined in claim 1, to form a compound of formula B',E,:

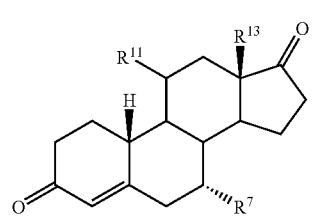

(b) nucleophilically substituting B',E at the 11-position with a halogenating agent if $R^{11}$ is not halogen, and (c) selectively reducing the halogenated compound B',E to a compound of formula III:

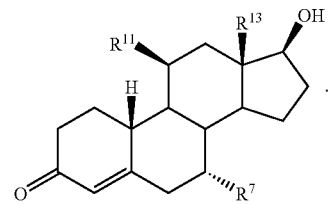

* * * * *

UNITED STATES PATENT AND TRADEMARK OFFICE
CERTIFICATE OF CORRECTION

PATENT NO. : 7,361,645 B2 Page 1 of 1
APPLICATION NO. : 10/467352
DATED : April 22, 2008
INVENTOR(S) : Rolf Bohlmann It is certified that error appears in the above-identified patent and that said Letters Patent is hereby corrected as shown below:

Title page, Item (86) "Feb 4, 2002" should read --Feb 4, 2004--
Column 19, Line 4 reads "–$R_{18}$" should read -- –$R^{18}$--
Column 19, Line 20 reads "Fluoro –17" should read --Fluoro –7--

Signed and Sealed this

Twenty-eighth Day of October, 2008

JON W. DUDAS
*Director of the United States Patent and Trademark Office*